(12) United States Patent
Jiang et al.

(10) Patent No.: US 10,921,228 B2
(45) Date of Patent: Feb. 16, 2021

(54) TESTING DEVICE AND METHOD FOR FLOATING RATE OF FLOATING AGENT FOR FRACTURE HEIGHT CONTROL

(71) Applicant: Southwest Petroleum University, Chengdu (CN)

(72) Inventors: Youshi Jiang, Chengdu (CN); Fujian Liu, Chengdu (CN); Yongming Li, Chengdu (CN); Bo Chen, Chengdu (CN); Jinzhou Zhao, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 16/747,492

(22) Filed: Jan. 20, 2020

(65) Prior Publication Data
US 2021/0018415 A1 Jan. 21, 2021

(51) Int. Cl.
*G01N 9/10* (2006.01)
*G05B 19/416* (2006.01)

(52) U.S. Cl.
CPC ............. *G01N 9/10* (2013.01); *G05B 19/416* (2013.01); *G05B 2219/41303* (2013.01)

(58) Field of Classification Search
CPC ................... G01N 9/10; G05B 19/416; G05B 2219/41303
USPC ...... 702/127, 137, 199; 73/32 R, 438, 53.01, 73/61.41, 61.42, 61.62, 61.63, 61.68, 73/61.69, 61.71, 64.56, 861, 861.05; 356/237.1, 256, 27, 28; 324/178; 348/61, 135
See application file for complete search history.

(56) References Cited

U.S. PATENT DOCUMENTS

| | | | |
|---|---|---|---|
| 2014/0080115 A1* | 3/2014 | Reed .................. | B01D 35/1475 435/3 |
| 2015/0276448 A1* | 10/2015 | Nyhart, Jr. ............ | G01F 1/7086 73/861.05 |
| 2016/0266023 A1* | 9/2016 | Gratiot ................... | G01N 15/10 |

FOREIGN PATENT DOCUMENTS

CN 108593502 A 9/2018

* cited by examiner

*Primary Examiner* — Robert R Raevis

(57) ABSTRACT

A testing device and method for floating rate of floating agent for fracture height control are provided. The test device includes a support frame, a glass tube vertically fixed on the support frame, a floating agent storage container, a control valve, and a liquid storage tank, wherein multiple circular holes are uniformly distributed along an axial direction of the glass tube, and multiple turbidimeters for measuring liquid turbidity are sequentially mounted on the circular holes. The liquid storage tank communicates with an inner cavity of an upper end of the glass tube through a pipeline, and the floating agent storage container is connected to an inner cavity of a lower end of the glass tube through a control valve. The present invention increases accuracy of measured floating rate of the floating agent, and provides reliable floating data of the floating agent for oil and gas reservoir reconstruction.

2 Claims, 3 Drawing Sheets

TESTING DEVICE AND METHOD FOR FLOATING RATE OF FLOATING AGENT FOR FRACTURE HEIGHT CONTROL

FIELD OF INVENTION

The present invention relates to the technical field of oil and gas field development, in particular, to a testing device and a method for floating rate of floating agent for fracture height control thereof.

BACKGROUND OF THE INVENTION

The carbonate reservoir in Shunbei Oilfield is characterized by deep burial, high temperature, and strong heterogeneity, and there are obvious abnormal bodies in the lower part of the wellbore. Acid fracturing is an effective method for increasing oil and gas production in carbonate reservoirs. However, due to the limitation of drilling technology, drilling wells are generally above the reservoir and far away, and conventional acid fracturing technology has a short downward extension distance for fractures, so that insufficient longitudinal extension of fractures will reduce the acid fracturing fractures to communicate with long-distance reservoirs below, which is not conducive to stable production of a single well. The acid fracturing technology with fractures extending downward can improve the effect of carbonate fracturing.

Current acid fracturing technology with carbonate fractures extending downward mainly uses hollow glass microspheres as the floating agent for fracture height control. When the floating agent enters the acid-etched fracture, it will float upwards and gather, forming a low-permeability layer on the top of the fracture, further blocking the upward passage of the fracture, forcing the acid fracturing fractures to extend downwards to communicate with the lower reservoirs to increase production. The floating rate of the floating agent for fracture height control affects the formation of artificial compartments. If the floating agent rises too fast, it will float a lot before reaching a predetermined position, and it is not easy to fully form an artificial compartment at the predetermined position, leading to weakened barrier effect of artificial compartment. If the floating rate of the floating agent is too slow, it will remain in the carrier liquid when reaching the destination and remain floating, and then the floating agent will lose the barrier function of forming an artificial barrier. Therefore, determining the floating rate of the floating agent is important for optimizing the floating agent and optimizing the construction displacement and the amount of the floating agent.

The current measuring method for the floating rate of the floating agent is mainly the "visual observation method". The "visual observation method" uses the naked eye to observe the floating process of the floating agent on a vertical measuring cylinder, and records the total time for most of the floating agent particles to float a certain distance in the liquid, so as to obtain the floating rate. This method cannot continuously measure the floating rate of the floating agent and is unsuitable for quantitatively determining the floating rate of the floating agent. Further, for solid-liquid two-phase mixtures in which the floating agent has the same color as the carrier liquid, the observation method is not applicable.

The existing measuring methods for the floating rate of the floating agent have some shortcomings. At present, there is no suitable method and device for testing the floating rate of the floating agent. To overcome the disadvantages of the existing detecting devices and methods for the floating rate of the floating agent, the present invention provides a set of new testing device and method for floating rate of floating agent for fracture height control.

SUMMARY OF THE INVENTION

In order to overcome drawbacks in the prior art, the present invention provides a testing device and method for floating rate of floating agent for fracture height control. In the present invention, by accurately monitoring the change of the turbidity of the liquid in the plexiglass tube with a turbidimeter, accurate judgment of critical moment of floating agent and accurate calculation of floating rate are realized, so as to overcome the error of judging the change of the turbidity of the liquid based on the color with the naked eye. The present invention is reliable in principle, simple in operation, increases the accuracy of the measured floating rate of the floating agent, and provides reliable floating data for indoor evaluation and practical application of the floating agent for oil and gas reservoir reconstruction, thereby having broad market prospects.

The technical solution of the present invention to solve above technical problems are as follows: a testing device for floating rate of floating agent for fracture height control includes a support frame, a glass tube vertically fixed on the support frame, a floating agent storage container, a control valve A, and a liquid storage tank, wherein a plurality of circular holes are uniformly distributed along an axial direction of the glass tube, and a plurality of turbidimeters for measuring liquid turbidity are mounted on the plurality of circular holes; the liquid storage tank communicates with an inner cavity of an upper end of the glass tube through a pipeline, and the floating agent storage container is connected to an inner cavity of a lower end of the glass tube through the control valve A.

In one embodiment, a control valve B is disposed between the glass tube and the liquid storage tank.

In one embodiment, the control valve A is a two-way valve, and two ends of the control valve A are respectively connected to the floating agent storage container and the inner cavity of the lower end of the glass tube.

In one embodiment, the testing device further includes a turbidity data processing system electrically connected to the turbidimeter.

In one embodiment, the circular holes have five circular holes, which are uniformly distributed, and an interval between the circular holes is 200 mm.

In one embodiment, the glass tube is a plexiglass tube.

A testing method for floating rate of floating agent for fracture height control includes steps of:

step A: turning off the control valve A and the control valve B, loading a floating agent for fracture height control into the floating agent storage container, and injecting distilled water into the liquid storage tank;

step B: turning on the control valve B, filling the glass tube with distilled water, and recording turbidity data $z_{10}$, $z_{20}$, $z_{30}$, $z_{40}$, and $z_{50}$ of the five turbidimeters before the test;

step C: turning on the control valve A so that the floating agent contacts the distilled water in the glass tube, initiating the floating process, and using a current time, at which the floating agent is contacting the distilled water in the glass tube, as an initial floating time $t_0$;

step D: recording the turbidity data of the five turbidimeters at intervals during the floating process, denoting a turbidity data of the n-th turbidimeter at the i-th time $t_i$ as $z_{ni}$;

step E: plotting a curve of turbidity over time monitored by each of the turbidimeters $z_{nt}=f(t)$, and determining time $t_{nf}$ at which a turbidity value at each of the turbidimeters starts to change and time $t_{nl}$ at which the turbidity value returns to a reference value after reaching a peak according to the curve;

step F: using following formula to calculate the floating rate of the floating agent according to the time data $t_{nf}$ and $t_{nl}$ of each of the turbidimeters:

$$\begin{cases} u_{nf} = \dfrac{D_n}{t_{nf} - t_0} \\ u_{nl} = \dfrac{D_n}{t_{nl} - t_0} \end{cases};$$

wherein $u_{nf}$ is a maximum floating rate of the floating agent calculated based on the data of the n-th turbidimeter, in mm/s; $u_{ni}$ is a minimum floating rate of the floating agent calculated based on the data of the n-th turbidimeter, in mm/s; $D_n$ is a floating distance of the floating agent corresponding to the n-th turbidimeter, in mm; to is an initial time when the floating agent floats during the test, in s; $t_{nf}$ is a time when the turbidity value at the n-th turbidimeter starts to change from the reference value, in s; $t_{nl}$ is a time when the turbidity value at the n-th turbidimeter returns to the reference value after reaching the peak, in s;

step G: averaging the maximum floating rate and the minimum floating rate of the floating agent calculated based on each turbidimeter data to obtain an average maximum floating rate $u_{max}$ and an average minimum floating rate $u_{min}$ of the floating agent:

$$u_{max} = \left(\sum_{n=1}^{N} u_{nf}\right) / N;$$

$$u_{min} = \left(\sum_{n=1}^{N} u_{nl}\right) / N;$$

wherein N is the number of the turbidimeters, dimensionless; $u_{nf}$ is a maximum floating rate of the floating agent calculated based on the data of the n-th turbidimeter, in mm/s; $u_{nl}$ is a minimum floating rate of the floating agent calculated based on the data of the n-th turbidimeter, in mm/s; $u_{max}$ is the average maximum floating rate, in mm/s; $u_{min}$ is the average minimum floating rate, in mm/s.

In one embodiment, the floating agent for fracture height control has a particle size of 70-200 mesh, and a bulk density of 0.33 g/cm3.

The present invention has the following beneficial effects: the prevent invention avoids the observation error caused by artificially judging the change of liquid turbidity by color, because the color of the low concentration floating agent in distilled water is relatively light, which is likely to cause an error in the determination of liquid turbidity; the quantitative and continuous monitoring of the liquid turbidity in the plexiglass tube during the floating process of the floating agent is realized, so that the calculation of the floating rate of the floating agent is more accurate; and the present invention may be applied in hydraulic fracturing process, theory in fracture height control of the acid fracturing process, and determination of the floating rate of the floating agent in the field of process technology research, with the measurement results that are more accurate and reliable and having higher practical value.

BRIEF DESCRIPTION OF THE DRAWINGS

Aspects of the present invention are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DESCRIPTION OF THE PREFERRED EMBODIMENTS

Figure 1:
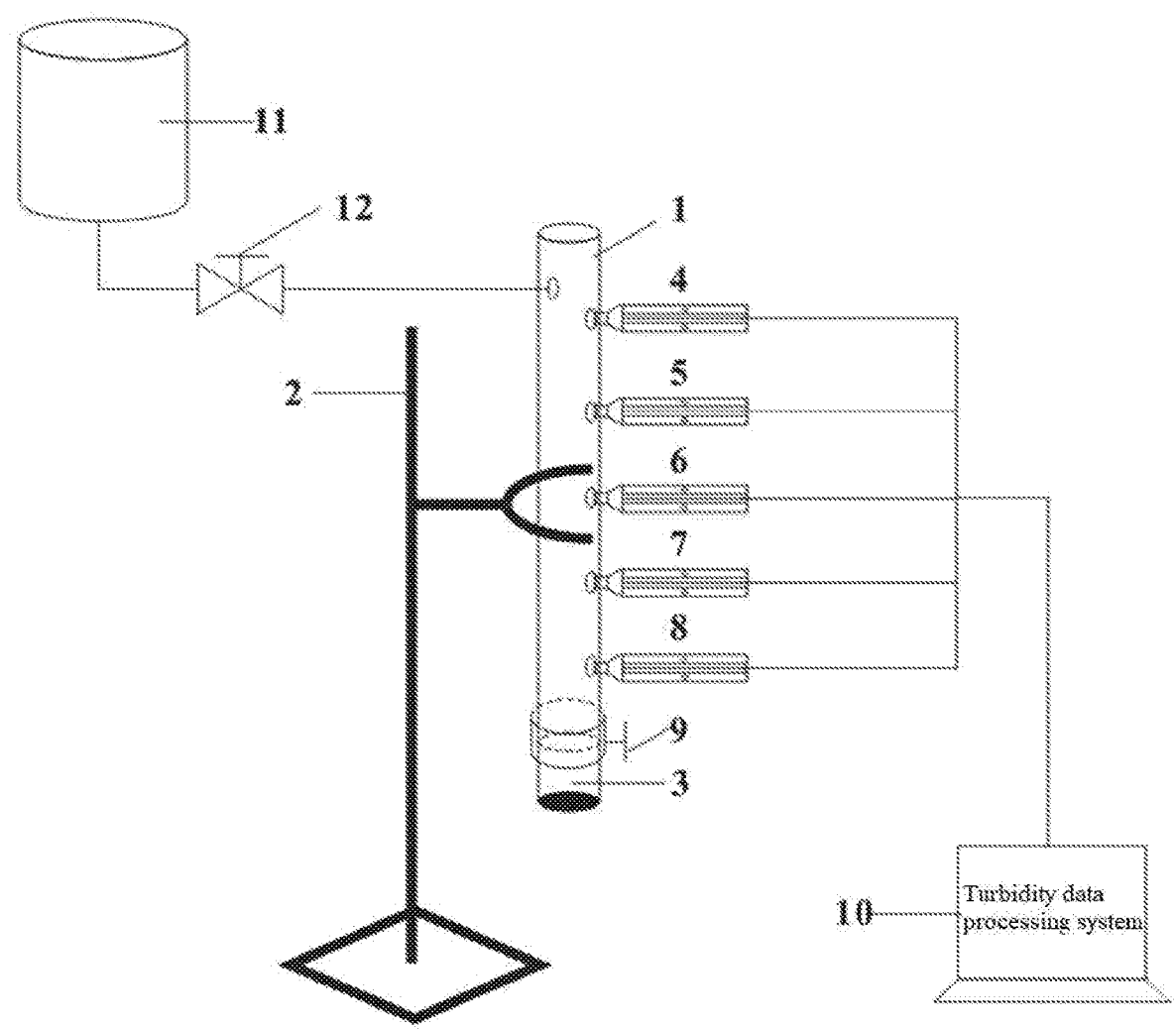
FIG. 1 is a structural diagram of a testing device for floating rate of floating agent for fracture height control according to an embodiment of the present invention.

The following invention provides different embodiment, or examples, for implementing different features of the provided subject matter. Specific examples of components and arrangements are described below to simplify the present invention. These are, of course, merely examples and are not intended to be limiting. For example, the formation of a first feature over or on a second feature in the description that follows may include embodiment in which the first and second features are formed in direct contact, and may also include embodiment in which additional features may be formed between the first and second features, such that the first and second features may not be in direct contact. In addition, the present invention may repeat reference numerals and/or letters in the various examples. This repetition is for the purpose of simplicity and clarity and does not in itself dictate a relationship between the various embodiment and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The present invention will be further described in detail in combination with embodiments and drawings. In FIG. 1, a testing device for floating rate of floating agent for fracture height control of the present invention includes a support frame 2, two glass tubes 1 vertically fixed on the support frame 2 that have diameters of 1.4 m and 5 cm respectively, a floating agent storage container 3, a turbidity data processing system 10, and a liquid storage tank 11. Five circular holes are uniformly distributed along an axial direction of the glass tube 1, and five turbidimeters 4, 5, 6, 7, and 8 for measuring liquid turbidity are sequentially mounted on the five circular holes from top to bottom. The turbidity data processing system 10 is electrically connected to the above-mentioned five turbidimeters 4, 5, 6, 7, and 8 for collecting data. The liquid storage tank 11 communicates with an inner cavity of an upper end of the glass tube 1 through a pipeline, and the floating agent storage container 3 is connected to an inner cavity of a lower end of the glass tube 1 through a control valve A (9). A control valve B (12) is disposed between the glass tube 1 and the liquid storage tank 11.

In this embodiment, the control valve A9 is a two-way valve, and two ends of the control valve A are respectively connected to the floating agent storage container 3 and the inner cavity of the lower end of the glass tube 1.

The glass tube 1 is filled with distilled water during test. The floating agent storage container 3 is loaded with a floating agent for fracture height control for fracturing before test, wherein the floating agent for fracture height control has a particle size of 70-200 mesh, and a bulk density of 0.33 g/cm$^3$.

In this embodiment, the glass tube 1 is a plexiglass tube.

The above-mentioned testing device is used to measure the floating rate of the floating agent in the carrier fluid, which provides basic parameters for the study of the fracture height control in the fault solution reservoir of an oil field.

Figure 2:
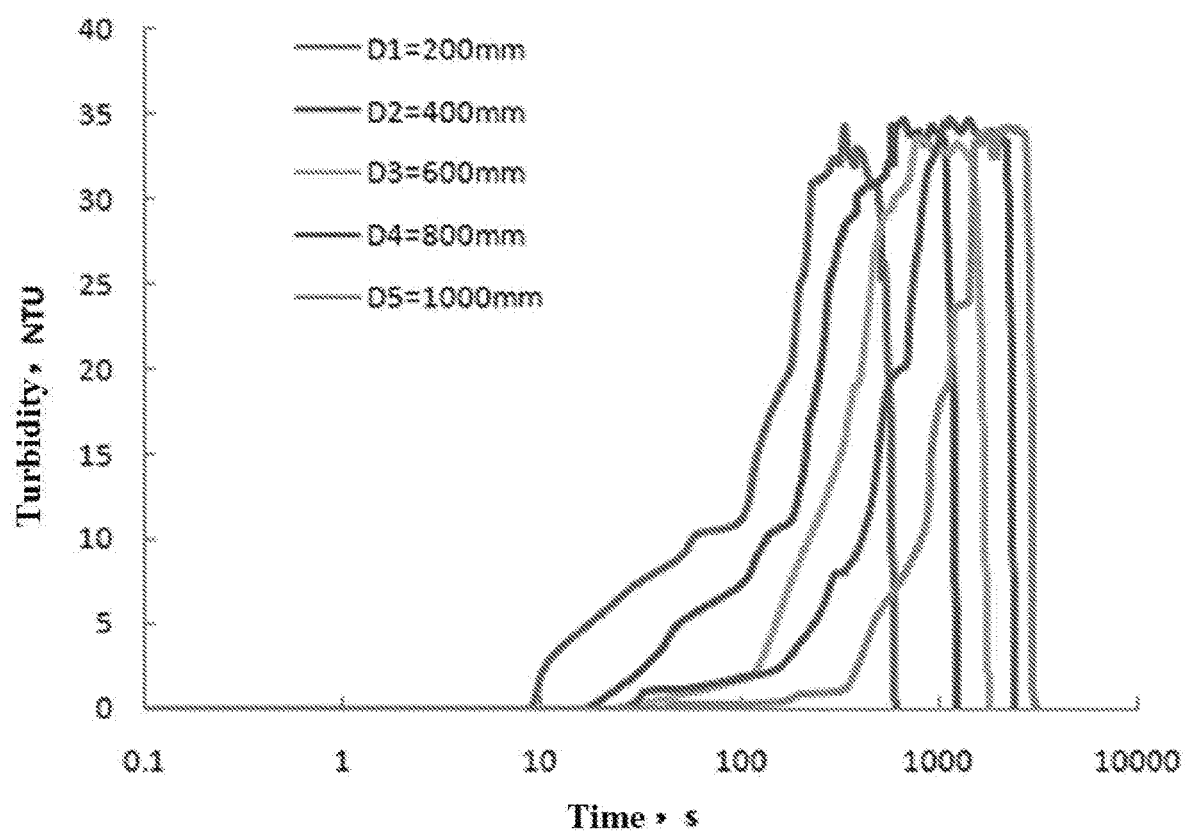
FIG. 2 is a curve of the relationship between liquid turbidity and time plotted in a rectangular coordinate system in Embodiment 1.
Figure 3:
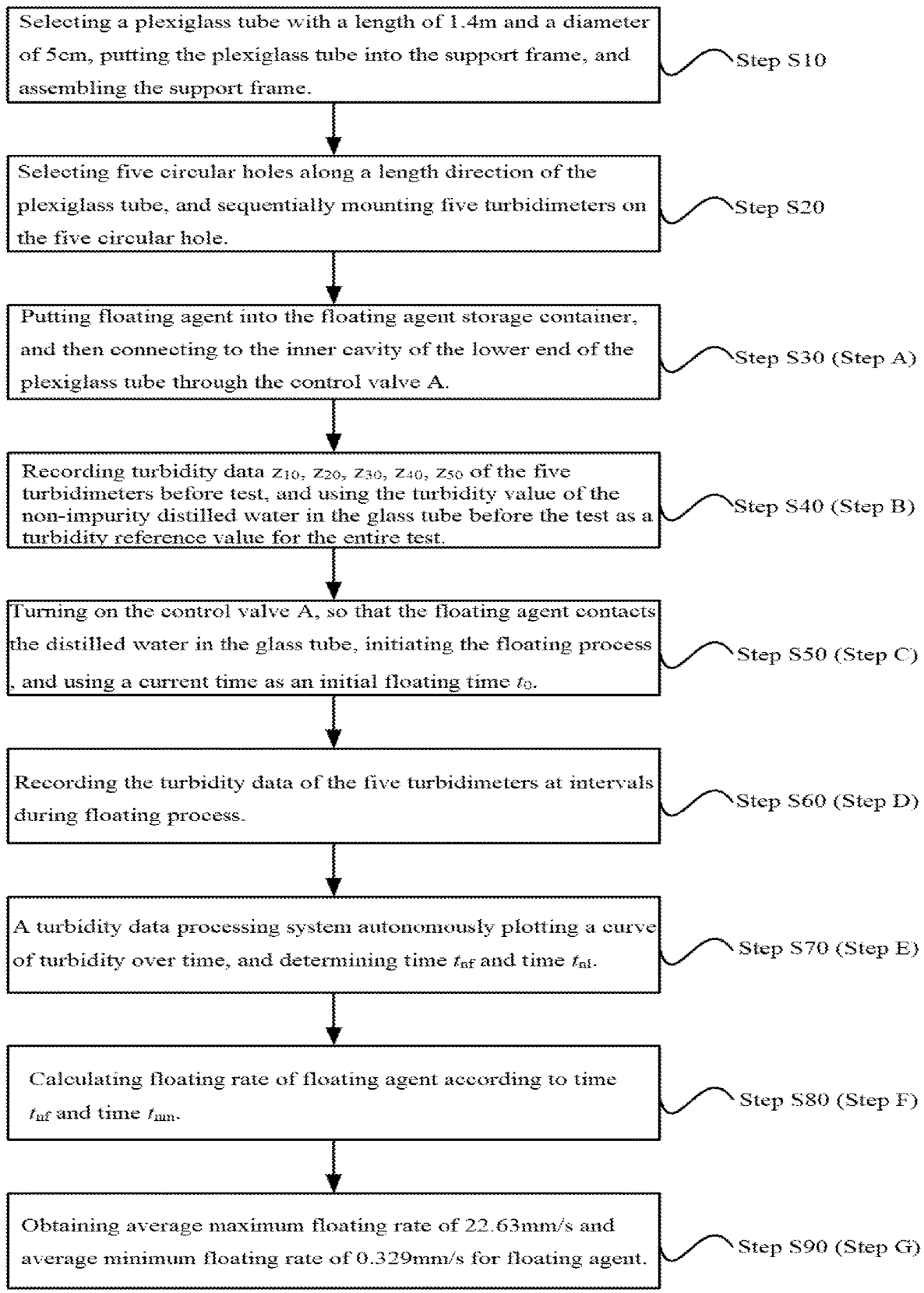
FIG. 3 is a flowchart of a method for floating rate of floating agent for fracture height control according to an embodiment of the present invention.

Please refer to FIG. 3. FIG. 3 is a flowchart of a method for floating rate of floating agent for fracture height control according to an embodiment of the present invention. The specific steps are as follows:

step S10, selecting a plexiglass tube with a length of 1.4 m and a diameter of 5 cm, putting the plexiglass tube into the support frame 2, and assembling the support frame 2;

step S20, selecting 5 equidistant circular holes along a length direction of the plexiglass tube, sequentially mounting five turbidimeters 4, 5, 6, 7, and 8 that are used for determining liquid turbidity on the five circular holes, and then connecting the pipeline;

step S30, taking the floating agent for fracture height control with a weight of 60 grams, putting it into the floating agent storage container 3, and then connecting to the inner cavity of the lower end of the plexiglass tube through the control valve A;

step S40, before turning on the control valve A, recording turbidity data $z_{10}$, $z_{20}$, $z_{30}$, $z_{40}$, $z_{50}$ of the five turbidimeters before the test, and using the turbidity value of the non-impurity distilled water in the glass tube before the test as a turbidity reference value for the entire test, wherein the floating distances of the floating agent corresponding to the five turbidimeters are 200 mm, 400 mm, 600 mm, 800 mm, and 1000 mm, respectively;

step S50, turning on the control valve A, so that the floating agent contacts the distilled water in the glass tube, initiating the floating process, and using a current time as an initial floating time $t_0$;

step S60, recording the turbidity data of the five turbidimeters at intervals during the floating process, denoting a turbidity data of the n-th turbidimeter at the i-th time $t_i$ as $z_{ni}$;

step S70, a turbidity data processing system taking time t as the abscissa and turbidity Z as the ordinate, autonomously plotting a curve of turbidity over time monitored by each of the turbidimeters $z_{nf}$=f (t) (as shown in FIG. 2), and determining a time $t_{nf}$ at which a turbidity value at each of the turbidimeters starts to change and a time $t_{nl}$ at which the turbidity value returns to a reference value after reaching a peak according to the curve;

Step S80, using the following formula (1) to calculate the floating rate of the floating agent according to the time data $t_{nf}$ and $t_{nm}$ of each of the turbidimeters:

$$\begin{cases} u_{nf} = \dfrac{D_n}{t_{nf} - t_0} \\ u_{nl} = \dfrac{D_n}{t_{nl} - t_0} \end{cases} ; \qquad (1)$$

wherein $u_{nf}$ is a maximum floating rate of the floating agent calculated based on the data of the n-th turbidimeter, in mm/s; $u_{nl}$ is a minimum floating rate of the floating agent calculated based on the data of the n-th turbidimeter, in mm/s; $D_n$ is a floating distance of the floating agent corresponding to the n-th turbidimeter, in mm; to is an initial time when the floating agent floats during the test, in s; $t_{nf}$ is a time when the turbidity value at the n-th turbidimeter starts to change from the reference value, in s; $t_{nl}$ is a time when the turbidity value at the n-th turbidimeter returns to the reference value after reaching the peak, in s;

Step S90, averaging the maximum floating rate and the minimum floating rate of the floating agent calculated based on each turbidimeter data (as shown in Table 1) to obtain an average maximum floating rate of 22.63 mm/s and an average minimum floating rate of 0.329 mm/s for the floating agent:

$$u_{max} = \left(\sum_{n=1}^{N} u_{nf}\right)/N; \qquad (2)$$

$$u_{min} = \left(\sum_{n=1}^{N} u_{nl}\right)/N; \qquad (3)$$

wherein N is the number of the turbidimeters, dimensionless; $u_nf$ is a maximum floating rate of the floating agent calculated based on the data of the n-th turbidimeter, in mm/s; $u_{ni}$ is a minimum floating rate of the floating agent calculated based on the data of the n-th turbidimeter, in mm/s; $u_{max}$ is the average maximum floating rate, in mm/s; $u_{min}$ is the average minimum floating rate, in mm/s.

Please note that, in FIG. 3, step 30 can be referred as step A, step 40 can be referred as step B, step 50 can be referred as step C, step 60 can be referred as step D, step 70 can be referred as step E, step 80 can be referred as step F, and step 90 can be referred as step G.

TABLE 1

| No. | floating distance (mm) | time $t_{nf}$ at which turbidity value starts to change (s) | time $t_{nl}$ at which turbidity value returns to reference value after reaching peak (s) | maximum floating rate (mm/s) | minimum floating rate (mm/s) |
|---|---|---|---|---|---|
| 1 | 200 | 9 | 610 | 22.22 | 0.328 |
| 2 | 400 | 17 | 1224 | 23.53 | 0.327 |
| 3 | 600 | 28 | 1795 | 21.43 | 0.334 |
| 4 | 800 | 33 | 2405 | 24.24 | 0.333 |

TABLE 1-continued

| No. | floating distance (mm) | time $t_{nf}$ at which turbidity value starts to change (s) | time $t_{nl}$ at which turbidity value returns to reference value after reaching peak (s) | maximum floating rate (mm/s) | minimum floating rate (mm/s) |
|---|---|---|---|---|---|
| 5 | 1000 | 46 | 3101 | 21.74 | 0.322 |
| Average value | | | | 22.63 | 0.329 |

What is described above does not limit the present invention in any form. The preferred embodiments are used to disclose the present invention as above but not to limit the present invention. Those skilled in the art may utilize the disclosed technical contents to make some alterations and modifications as equivalent embodiments of equal changes without departing form the scope of the technical scheme of the present invention and any simple alterations, equivalent changes and modifications made according to the technical essence of the present invention without departing from the technical contents of the present invention should be contained in the scope of the technical scheme of the present invention.

What is claimed is:

1. A testing method for floating rate of floating agent for fracture height control, comprising steps of:

step A: turning off a control valve A and a control valve B, loading a floating agent for fracture height control into a floating agent storage container, and injecting distilled water into a liquid storage tank;

step B: turning on the control valve B, filling a glass tube with the distilled water, and recording turbidity data $z_{10}$, $z_{20}$, $z_{30}$, $z_{40}$, and $z_{50}$ of five turbidimeters before test;

step C: turning on the control valve A so that the floating agent contacts the distilled water in the glass tube, initiating a floating process, and using a current time, at which the floating agent is contacting the distilled water in the glass tube, as an initial floating time t0;

step D: recording the turbidity data of the five turbidimeters at intervals during the floating process, denoting a turbidity data of the n-th turbidimeter at the i-th time $t_i$ as $z_{ni}$;

step E: plotting a curve of turbidity over time monitored by each of the turbidimeters $z_{nt}=f(t)$, and determining a time $t_{nf}$ at which a turbidity value at each of the turbidimeters starts to change and a time $t_{nl}$ at which the turbidity value returns to a reference value after reaching a peak according to the curve;

step F: using following formula to calculate a floating rate of the floating agent according to time data $t_{nf}$ and $t_{nl}$ of each of the turbidimeters:

$$\begin{cases} u_{nf} = \dfrac{D_n}{t_{nf} - t_0} \\ u_{nl} = \dfrac{D_n}{t_{nl} - t_0} \end{cases};$$

wherein $u_{nf}$ is a maximum floating rate of the floating agent calculated based on the data of the n-th turbidimeter, in mm/s; $u_{nl}$ is a minimum floating rate of the floating agent calculated based on the data of the n-th turbidimeter, in mm/s; $D_n$ is a floating distance of the floating agent corresponding to the n-th turbidimeter, in mm; $t_0$ is an initial time when the floating agent floats during test, in s; $t_{nf}$ is a time when the turbidity value at the n-th turbidimeter starts to change from the reference value, in s; $t_{nl}$ is a time when the turbidity value at the n-th turbidimeter returns to the reference value after reaching the peak, in s;

step G: averaging the maximum floating rate and the minimum floating rate of the floating agent calculated based on each turbidimeter data to obtain an average maximum floating rate $u_{max}$ and an average minimum floating rate $u_{min}$ of the floating agent:

$$u_{max} = \left(\sum_{n=1}^{N} u_{nf}\right) \bigg/ N;$$

$$u_{min} = \left(\sum_{n=1}^{N} u_{nl}\right) \bigg/ N;$$

wherein N is a number of the turbidimeters, dimensionless; $u_{nf}$ is the maximum floating rate of the floating agent calculated based on the data of the n-th turbidimeter, in mm/s; $u_{nl}$ is the minimum floating rate of the floating agent calculated based on the data of the n-th turbidimeter, in mm/s; $u_{max}$ is the average maximum floating rate, in mm/s; $u_{min}$ is the average minimum floating rate, in mm/s.

2. The testing method for floating rate of floating agent for fracture height control of claim 1, wherein the floating agent for fracture height control has a particle size of 70-200 mesh, and a bulk density of 0.33 g/cm$^3$.

* * * * *